United States Patent
Nakagawa et al.

(10) Patent No.: US 7,018,613 B2
(45) Date of Patent: Mar. 28, 2006

(54) PREPARATIONS FOR EVALUATING ELIMINATIVE ABILITY OF STOMACH

(75) Inventors: Shinsuke Nakagawa, Tokushima (JP); Keigo Yamada, Tokushima (JP); Masateru Miyake, Tokushima (JP); Makoto Inada, Tokushima (JP); Nobuhiro Ikei, Tokushima (JP); Atsunari Noda, Tokushima (JP); Hideji Nonomura, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 260 days.

(21) Appl. No.: 10/275,072

(22) PCT Filed: Apr. 25, 2001

(86) PCT No.: PCT/JP01/03549

§ 371 (c)(1),
(2), (4) Date: Feb. 25, 2003

(87) PCT Pub. No.: WO01/82979

PCT Pub. Date: Nov. 8, 2001

(65) Prior Publication Data

US 2003/0190283 A1 Oct. 9, 2003

(30) Foreign Application Priority Data

May 2, 2000 (JP) .............................. 2000-133691

(51) Int. Cl.
*A61K 51/00* (2006.01)

(52) U.S. Cl. ......................... 424/1.81; 424/9.1; 424/9.2
(58) Field of Classification Search ............... 424/1.81, 424/9.1, 9.2, 9.3
See application file for complete search history.

(56) References Cited

U.S. PATENT DOCUMENTS

| | | | | |
|---|---|---|---|---|
| 4,830,010 A | * | 5/1989 | Marshall | 600/300 |
| 5,707,602 A | * | 1/1998 | Klein | 424/1.17 |
| 6,113,875 A | * | 9/2000 | Nystrom et al. | 424/1.29 |
| 6,186,958 B1 | * | 2/2001 | Katzman et al. | 600/532 |
| 6,294,151 B1 | * | 9/2001 | Hayakawa et al. | 424/1.81 |
| 6,509,002 B1 | * | 1/2003 | Kohno et al. | 424/1.81 |
| 6,740,305 B1 | * | 5/2004 | Ajami | 424/9.1 |

FOREIGN PATENT DOCUMENTS

| | | |
|---|---|---|
| EP | 0860170 A1 | 8/1998 |
| WO | WO 96/36330 | 11/1996 |
| WO | WO 97/35622 | 10/1997 |

* cited by examiner

*Primary Examiner*—Michael Hartley
(74) *Attorney, Agent, or Firm*—Finnegan, Henderson, Farabow, Garrett & Dunner, LLP

(57) ABSTRACT

Preparations whereby reduction or acceleration of the gastric emptying rate can be noninvasively evaluated: and a method of evaluating the gastric emptying rate by using these preparations. Thus, reduction or acceleration of the gastric emptying rate can be safely and conveniently examined. Namely, theses preparations are useful in objectively diagnosing the gastric motor function, as well as in evaluating and judging the drug effect or therapeutic effect of a drug concerning the gastric motor function on individual patients.

20 Claims, 4 Drawing Sheets

F I G. 2
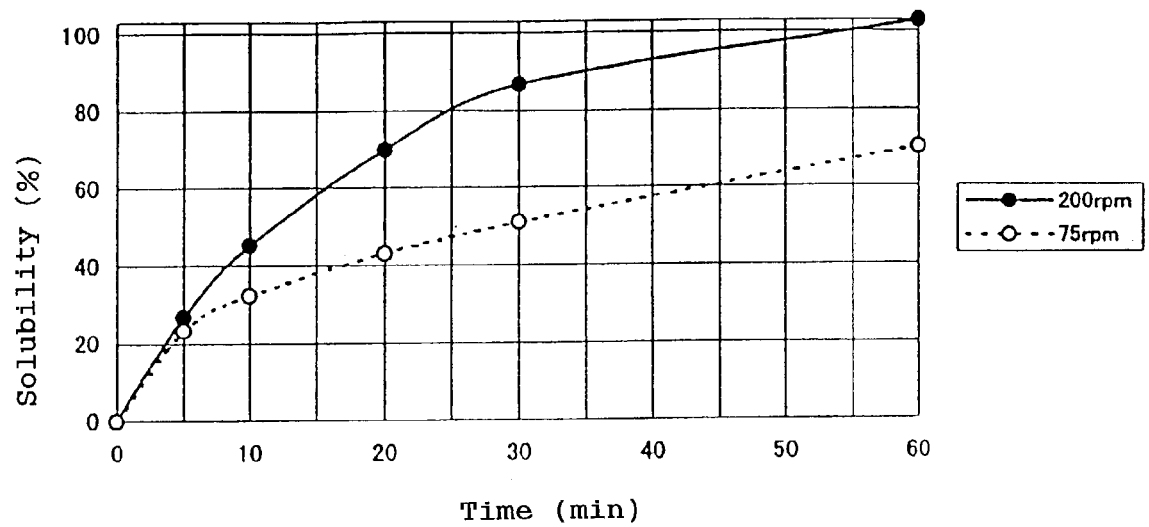

F I G. 3
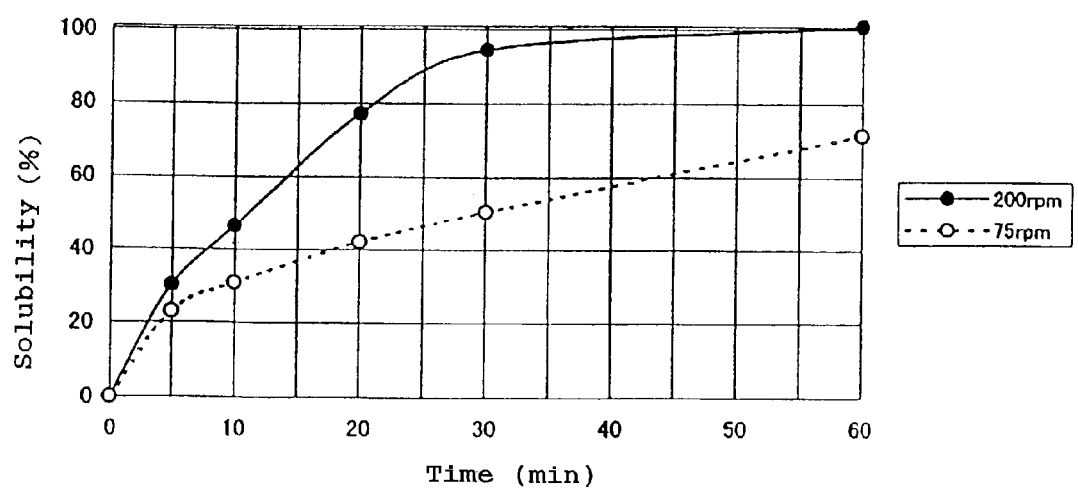

PREPARATIONS FOR EVALUATING ELIMINATIVE ABILITY OF STOMACH

TECHNICAL FIELD

The present invention relates to a technique for the diagnostic measurement of the gastric emptying rate. More specifically, the present invention relates to a preparation which can measure the reduction or acceleration of the gastric emptying rate in a noninvasive manner using the expired air, and a method for measuring the gastric emptying rate using the preparation.

The present invention allows the safe and easy examination of reduction or acceleration of the gastric emptying rate. Specifically, the preparation of the present invention is useful for the objective diagnosis of the gastric motor function, and are useful for evaluating the pharmacological effects or therapeutic effects of drugs relating to the gastric motor function in individual subjects.

BACKGROUND ART

In the field of internal medicine, the treatment of stomach ulcer and duodenal ulcer has made a great transition from treatment by means of surgical procedures to noninvasive drug treatments as a result of progress made in drugs such as $H_2$-antagonists, gastric inhibitors and the like.

On the other hand, there has been an increase in subjects who, while showing no signs of ulcer in endoscopic examinations, nevertheless complain of symptoms such as vomiting, nausea, gastric fullness, heavy stomach, heartburn, anorexia, upper abdominal pain and the like (such subject is referred to collectively as "subjects with indefinite complaint"). Such indefinite complaint is generally diagnosed on the basis of the symptoms reported by the subject, and it is extremely difficult to diagnose such complaint in an objective and quantitative manner. Furthermore, the difficulty of such diagnosis delays appropriate treatment, and also causes a deterioration in the quality of life (QOL) of such subject with indefinite complaint. It has recently been found that such indefinite complaint reported by subject have a close correlation with a lowering of the gastric emptying rate (GER), and it has been reported that a lowering of the gastric emptying rate is observed in approximately half of all subjects suffering from indefinite complaints.

Accordingly, it would appear that if it were possible to measure the gastric emptying rate easily and with high precision without imposing a burden on the subject, this would make a great contribution to the appropriate diagnosis and treatment of the subject suffering from indefinite complaint.

However, conventional methods for measuring the gastric emptying rate are expensive, or are invasive so that such methods impose a psychological and physical burden on the subject. Moreover, the time for which the subject is constrained is long in the case of such methods, and the measurement precision is insufficient. For example, among conventional methods for measuring the gastric emptying rate, the isotope method (e.g., scintigraphy or the like) uses a radioactive isotope; as a result, the administration of this method is complicated. Furthermore, since this method requires an expensive γ-ray camera, the use of this method is restricted to special facilities. Furthermore, in the case of the X-ray impermeable marker method, the marker is not discharged from the stomach simultaneously with the food contents, but is instead discharged from the stomach after all of the food contents have bee discharged; as a result, the actual gastric emptying function cannot be accurately examined. Furthermore, in the case of the acetaminophen method, there is a danger of drug allergy and liver damage due to the side effects of acetaminophen; furthermore, since this drug is subject to other effects in the body such as absorption in the small intestine, metabolization by the liver, excretion from the kidneys and the like, the gastric emptying function cannot be accurately examined. Furthermore, since the concentration of acetaminophen in the blood is measured after administering acetaminophen, the invasive procedure of blood collection is required.

Furthermore, methods such as a method in which the endogastric volume and saburra are measured by means of ultrasonic waves (ultrasound method), a method in which the gastric emptying rate is measured by MRI (magnetic resonance imaging method), a method in which the gastric motor function is evaluated by measuring an electrogastrogram (elctrogastrography) and the like have also been proposed as other methods for measuring the gastric emptying rate; however, such methods suffer from the following problems: (i) There are problems in the precision of the diagnostic method, (ii) there are no fixed criteria, so that evaluations vary according to the evaluator, and (iii) the subject must be constrained for a long period of time while the diagnosis is being made.

DISCLOSURE OF THE INVENTION

It is an object of the present invention to provide a preparation that allows the easy and noninvasive measurement of the gastric emptying function. More concretely, it is an object of the present invention to provide a preparation that allows the measurement and evaluation of the gastric emptying rate using the expired air. Furthermore, it is also an object of the present invention to provide a simple method for measuring the gastric emptying rate using the above-mentioned preparation. Moreover, it is also an object of the present invention to provide a method for diagnosing and evaluating the gastric emptying function (gastric motor function) in examined subjects, and a method for evaluating the pharmacological effects and therapeutic effects of drugs relating to the gastric motor function in individual subjects, utilizing the abovementioned method for measuring the gastric emptying rate.

Generally, when food is consumed and enters the stomach, it is gradually physically pulverized into small particles as a result of being subjected to the effects of gastric contractions (gastric peristalsis), as well as the effects of acids and enzymes. Then, at the point in time at which the food has been converted into particle with a size of approximately 1 to 2 mm, this food is transferred into the intestines via the pylorus. The present inventors focused on the mechanism of the gastric digestion and evacuation, to develop a method for the simple measurement of the gastric emptying rate. As a result, the present inventors found that in the case of a preparation (a stomach-soluble type <a disintegrate-release type sustained-release preparation>) that is prepared so that is gradually disintegrated and dissolved inside the stomach, there is a correlation between the endogastric elution behavior of the components of the preparation and the gastric emptying rate (gastric movement). On the basis of this finding, the present inventors confirmed that the gastric emptying rate can easily be measuring the elution behavior of the disintegrate-release type sustained-release preparation. Furthermore, the present inventors confirmed that, when a labeled compound excreted in the exhalation as carbon dioxide gas following metabolization is used in preparation of the abovementioned sustained-release preparation, the gastric emptying rate can be measured in a noninvasive manner from the excretion behavior of the labeled compound or metabolites thereof.

The first preparation of the present invention (hereafter referred to as "a stomach-soluble preparation") was perfected on the basis of such findings. Specifically, the first preparation of the present invention ("a stomach-soluble preparation") is a preparation for measuring the gastric emptying rate as described in items 1 through 9 below:

Item 1. A preparation for measuring the gastric emptying rate comprising a composition containing a compound (labeled compound) that is labeled with either an isotope of C or O, or with isotopes of both, and that is converted into labeled $CO_2$ in the body and excreted in the exhalation, this preparation being a disintegrate-release type sustained-release preparation.

Item 2. The preparation for measuring the gastric emptying rate according to item 1, wherein the behavior of the preparation following oral administration to the subject is such that:
(i) the preparation remains inside the stomach for a certain period of time after entering the stomach, without being immediately discharged from the stomach,
(ii) the surface of the preparation is gradually eroded by the gastric contraction so that the preparation is disintegrated, and as this erosion and disintegrate occurs, the labeled compound is gradually eluted into the stomach, and
(iii) the eluted labeled compound is converted into labeled carbon dioxide gas inside the stomach and excreted in the exhalation, or is absorbed, metabolized and excreted in the exhalation as labeled carbon dioxide gas.

Item 3. The preparation for measuring the gastric emptying rate according to item 1 or item 2, wherein the preparation can expand to a size that does not pass through the pylorus for a certain period of time following oral administration.

Item 4. The preparation for measuring the gastric emptying rate according to any of items 1 through 3, which comprises an anti-disintegrator in addition to a labeled compound.

Item 5. The preparation for measuring the gastric emptying rate according to item 4, wherein the anti-disintegrator is at least one member selected from a group consisting of water-soluble high-molecular weight compound, fat and oil, and sugars.

Item 6. The preparation for measuring the gastric emptying rate according to item 4 or item 5, wherein the anti-disintegrator is at least one member selected from a group consisting of hydroxypropylcellulose, hydroxypropylmethylcellulose, ethylcellulose, cellulose acetate phthalate, hardened oil, carnauba wax, sugars and sugar alcohol.

Item 7. The preparation for measuring the gastric emptying rate according to any of items 1 through 6, wherein the isotope is at least one member selected from a group consisting of $^{13}C$, $^{14}C$ and $^{18}O$.

Item 8. The preparation for measuring the gastric emptying rate according to any of items 1 through 7, wherein the labeled compound is at least one member selected from a group consisting of alkali metal salt, alkaline earth metal salt and ammonium salt of carbonic acid, alkali metal hydrogencarbonate, alkaline earth metal hydrogencarbonate and ammonium hydrogencarbonate Item 9. The preparation for measuring the gastric emptying rate according to any of items 1 through 8, wherein the labeled compound is at least one member selected from a group consisting of acetic acid, glycine, octanoic acid and alkali metal salts thereof.

Furthermore, the preparation has a form for oral administration such as tablet, capsule, pill, powder, granule or the like.

As a result of further research based on the abovementioned findings, the present inventors found that if a labeled compound that generates carbon dioxide gas as result of dissolution or a metabolic reaction is used in manufacturing of a preparation that dissolves in the intestines, the preparation is be dissolved in intestine or be subjected to further metabolization, and excreted in the exhalation as labeled carbon dioxide gas. The inventors also found that the gastric emptying rate can be measured noninvasively by tracking the behavior of the labeled carbon dioxide gas excreted in the exhalation, and that as a result, the gastric emptying function can easily be evaluated.

There are generally two types of gastric and intestinal motor patterns (motor mode) in humans and animals, i.e., a fasting mode and an ingestion mode. The present inventors confirmed that the gastric emptying rate can be measured in accordance with these various motor modes by appropriately selecting the size of the abovementioned intestine-soluble preparation.

The second preparation of the present invention (hereafter referred to as "an intestine-soluble preparation") was perfected on the basis of such findings. Specifically, the second preparation of the present invention ("a intestine-soluble preparation") is a preparation for measuring the gastric emptying rate as described in items 10 through 15 below:

Item 10. A preparation for measuring the gastric emptying rate comprising a composition containing a compound (labeled compound) that is labeled with either an isotope of C or O, or with isotopes of both, and that is converted into labeled $CO_2$ in the body and excreted in the exhalation, the preparation being coated by an enteric coating.

Item 11. The preparation for measuring the gastric emptying rate according to item 10, wherein the behavior of the preparation following oral administration to the subject being such that:
(1) the preparation remains inside the stomach for a certain period of time after entering the stomach, without being discharged from the stomach,
(2) the preparation is discharged from the stomach by the gastric housekeeper movement, and
(3) the preparation is then dissolved in the intestines, and the labeled compound eluted from the interior of the preparation is converted into labeled carbon dioxide inside the intestines or absorbed and metabolized, and is excreted in the exhalation.

Item 12. The preparation for measuring the gastric emptying rate according to item 10, wherein the behavior of the preparation following oral administration to the subject being such that:
(1) the preparation enters the stomach,
(2) the preparation is discharged from the stomach by the gastric movement to discharge food, and
(3) the preparation is dissolved in the intestines, and the labeled compound eluted from the interior of the preparation is converted into labeled carbon dioxide inside the intestines or absorbed and metabolized, and is excreted in the exhalation.

Item 13. The preparation for measuring the gastric emptying rate according to any of items 10 through 12, wherein the isotope is at least one member selected from a group consisting of $^{13}C$, $^{14}C$ and $^{18}O$.

Item 14. The preparation for measuring the gastric emptying rate according to any of items 10 through 13, wherein the labeled compound is at least one compound selected from a group consisting of alkali metal salt, alkaline earth metal salt and ammonium salt of carbonic acid, alkali metal hydrogencarbonate, alkaline earth metal hydrogencarbonate, and ammonium hydrogencarbonate.

Item 15. The preparation for measuring the gastric emptying rate according to any of items 10 through 14, wherein the labeled compound is at least one compound selected from a group consisting of acetic acid, glycine, octanoic acid and alkali metal salts thereof.

The abovementioned preparation can be prepared in a form for oral administration such as tablet, capsule, pill, powder, granule or the like.

Furthermore, the present invention provides a method for measuring the gastric emptying rate using at least one preparation for measuring the gastric emptying rate, i.e., either the first preparation or the second preparation described above. In concrete terms, the method can be performed by orally administering any of the stomach-soluble preparations described in the abovementioned items 1 through 9 or the intestine-soluble preparations described in the abovementioned items 10 through 15 to the subject, and then measuring the behavior of the labeled compound in the body, or measuring the amount or behavior of a labeled compound (metabolite) excreted from the body. Preferably, this involves measurement of the amount or behavior of labeled $CO_2$ excreted in the exhalation.

The gastric emptying rate of the subject can be evaluated by utilizing such a method. Accordingly, the present invention also provides a diagnostic evaluation method for the gastric emptying rate of humans or animals. In concrete terms, this method can be performed by orally administering any of the stomach-soluble preparations described in the abovementioned items 1 through 9 or the intestine-soluble preparations described in the abovementioned items 10 through 15 to a subject for whom a reduction or acceleration of the gastric emptying function is suspected, and then comparing the behavior of the labeled compound inside the body or the amount or behavior of a labeled compound excreted from the body, with the behavior of the labeled compound inside the body or amount or behavior of a labeled compound excreted from the body that is obtained for a healthy subject using the same preparation for measuring the gastric emptying rate. Preferably, the method is performed by comparing the amount or behavior of labeled $CO_2$ excreted in the exhalation for the abovementioned healthy subject and subject in which a reduction or acceleration of the gastric emptying function is suspected. Furthermore, the evaluation of the abovementioned gastric emptying rate can be performed more accurately by using two separate preparations, i.e., the stomach-soluble preparation and the intestine-soluble preparation, in combination.

Furthermore, in the case of drugs relating to the gastric motor function, the pharmacological effect or therapeutic effect on individual subjects can be evaluated by utilizing the abovementioned method. Accordingly, the present invention also relates to a method for evaluating the pharmacological effect or therapeutic effect of drugs relating to the gastric motor function. In concrete terms, this method can be performed by orally administering any of the stomach-soluble preparations described in the abovementioned items 1 through 9 or the intestine-soluble preparations described in the abovementioned items 10 through 15 to the subject before and after the administration of a drug relating to the gastric motor function, measuring the behavior of the labeled compound inside the body or the amount or behavior of a labeled compound (matabolite) excreted from the body, and comparing the results obtained before the administration of the drug with the results obtained after the administration of the drug. Preferably, the method of the present invention is performed by comparing the amount or behavior of labeled $CO_2$ gas excreted in the exhalation prior to the administration of the abovementioned drug with the amount or behavior of labeled $CO_2$ gas excreted in the exhalation following the administration of the abovementioned drug. Furthermore, the evaluation of the pharmacological effect or therapeutic effect of the abovementioned drug can be performed more accurately by using two preparations, i.e., a stomach-soluble preparation and an intestine-soluble preparation, in combination.

BRIEF DESCRIPTION OF THE DRAWINGS

FIG. 2 is a graph which shows the elution behavior (solubility) obtained in a case where the sustained-release tablets of Example 6 (stomach-soluble tablets, 10 tablets) were tested in a test solution (pH 4.8) together with 100 g of beads in Test Example 1 (Japan Pharmacopoeia ($13^{th}$ Ed.), paddle method).

FIG. 3 is a graph which shows the elution behavior (solubility) obtained in a case where the sustained-release tablets of Example 6 (stomach-soluble tablets, 10 tablets) were tested in a test solution (pH 4.8) together with 200 g of beads in Test Example 1 (Japan Pharmacopoeia ($13^{th}$ Ed.), paddle method).

Figure 1:
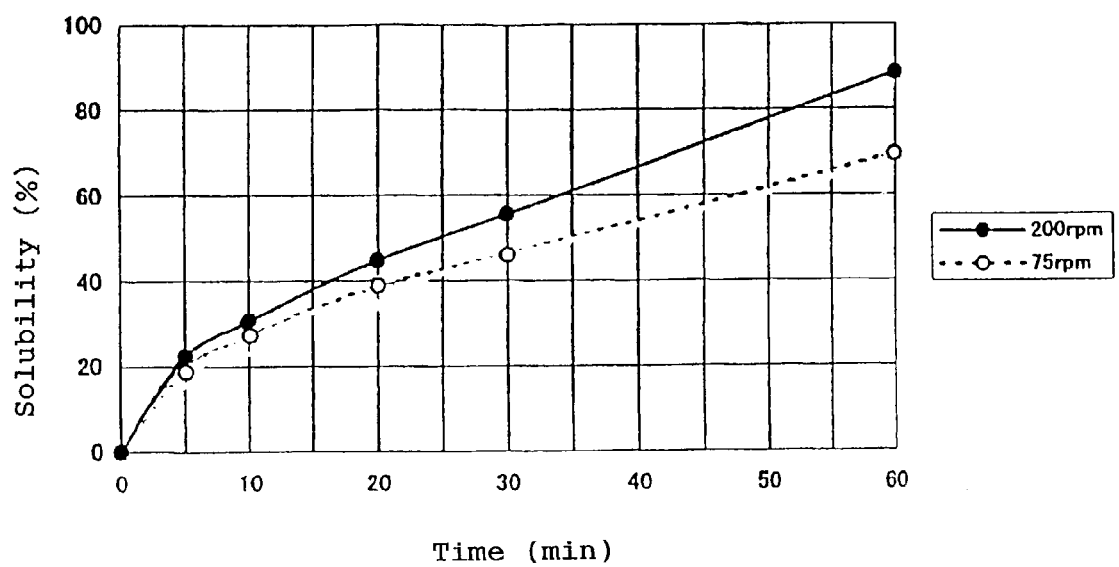
FIG. 1 is a graph which shows the elution behavior (solubility) obtained in a case where the sustained-release tablets of Example 6 (stomach-soluble tablets, 10 tablets) were tested alone in a test solution (pH 4.8) in Test Example 1 (Japan Pharmacopoeia ($13^{th}$ Ed.), paddle method). The horizontal axis indicates the dissolution time (minutes), while the vertical axis indicates the solubility (%) of the tablets. The open circles (-○-) indicate a case in which the paddle rpm was set at 75 rpm, and the closed circles (-●-) indicate a case in which the paddled rpm as set at 200 rpm (the same is true in FIGS. 2 and 3 below).

BEST MODE FOR CARRYING OUT THE INVENTION (1) First Preparation (Stomach-Soluble Preparation)

The first preparation of the present invention is a composition containing a compound which is labeled with an isotope of C or O, or with both isotopes, and which is converted into labeled $CO_2$ in the body and excreted in the exhalation; this preparation is used to measure the gastric emptying rate, which is prepared in the form of a sustained-release preparation that is disintegrated and released in the stomach (a disintegrate-release type sustained-release preparation).

There are no particular restrictions on the compound labeled with an isotope of C or O or isotopes of both that is used in the preparation for measuring the gastric emptying rate, as long as the compound is eluted and dissolved in the stomach following oral administration, and is subsequently disintegrated or metabolized in some cases, and excreted in the exhalation, urine or body fluids (blood, sputum, perspiration or the like).

A desirable example of such a compound is one which is converted into carbonate ions ($CO_3^{-2}$), hydrogencarbonate ions ($HCO_3^{-1}$) or carbon dioxide gas ($CO_2$) after being dissolved in the stomach, and after being subsequently disintegrated or metabolized in some cases, and which appears as carbon dioxide gas in the exhalation.

Compounds which dissolve and generate carbonate ions or hydrogencarbonate ions may be broadly cited as examples of compounds that quickly appear as carbon dioxide gas in the exhalation following dissolution; examples of such compounds include alkali metal carbonates such as sodium carbonate, potassium carbonate and the like; alkaline earth metal carbonates such as calcium carbonate, magnesium carbonate and the like; ammonium carbonate; alkali metal hydrogencarbonates such as potassium hydrogencarbonate, sodium hydrogencarbonate and the like; and ammonium hydrogencarbonate. Furthermore, especially if these compounds are used in combination with acidic compounds such as citric acid, tartaric acid, malic acid or the like, the compounds will quickly appear in the exhalation as carbon dioxide gas. Especially desirable for use are sodium carbonate, potassium carbonate, sodium hydrogencarbonate and potassium hydrogencarbonate.

Furthermore, amino acids, proteins, organic acids or salts thereof (e.g., alkali metal salts such as Na salts or the like), sugars, fats and the like may be cited as examples of compounds that appear as carbon dioxide gas in the exhalation after being dissolved inside the stomach and subsequently broken down or metabolized. After being digested and absorbed, all of these compounds generate carbon dioxide gas in the exhalation as a result of liver metabolism. Here, examples of amino acids that can be used include glycine, phenylalanine, tryptophan, methionine, valine, histidine and the like; examples of organic acids that can be used include acetic acid, lactic acid, pyruvic acid, butyric acid, octanoic acid, propionic acid and alkali metal salts of these acids; examples of sugars that can be used include glucose, galactose, xylose, lactose and the like; and examples of fats that can be used include medium-chain triglycerides such as trioctanoin or the like. However, the present invention is not limited to these compounds. Examples of compounds that are especially desirable for use include amino acids such as glycine or the like, organic acids such as acetic acid, octanoic acid or the like, and alkali metal salts of such organic acids (sodium salts or potassium salts).

Concrete examples of isotopes that can be used to label such compounds include $^{13}C$, $^{14}C$ and $^{18}O$. Such isotopes may be radioactive or non-radioactive; however, from the standpoint of safety, non-radioactive isotopes are preferable. In particular, $^{13}C$ is especially desirable for use as such an isotope.

There are no particular restrictions on the labeling method using these isotopes; commonly used methods may be widely employed. Furthermore, compounds which are known as labeled compounds that are labeled with these isotopes, and compounds that are commercially available, may be widely used (see Sasaki, "5.1 Use of Stable Isotopes in Clinical Diagnoses"; Kagaku no Ryoiki 107, "Use of Stable Isotopes in Medicine, Pharmacy and Biology", pp. 149–163 (1975) Nankodo; Kajiwara, RADIOISOTOPES, 41, 45–48 (1992) and the like).

The preparation for measuring the gastric emptying rate of the present invention (stomach-soluble preparation) is characterized in that it is a disintegrate-release type sustained-release preparation in solid form for oral administration, which comprises the abovementioned isotope-labeled compound or a composition containing the compound.

The disintegrate-release type sustained-release preparation is a preparation in which the release of the labeled compound containing the isotope (constituting the active ingredient of the preparation of the present invention) from the preparation is controlled by the disintegrate characteristics of the preparation; this term of "disintegrate-release type sustained-release preparation" is used in a sense that includes the preparation in which the labeled compound is gradually and continuously released and eluted as the preparation disintegrates. In cases where such a disintegrate-release type sustained-release preparation is orally administered, the surface of the preparation is gradually erodes by the gastric contraction movement so that the preparation is disintegrated, and as this erosive disintegrate occurs, the active disingredient contained in the preparation, i.e., the labeled compound, is gradually released into the stomach.

Such disintegrate-release type sustained-release preparations may include preparations that show zero-order release behavior in elution tests prescribed by the Japan Pharmacopoeia, as well as preparations that show zero-order release behavior in the stomach following oral administration (in vivo elution).

It is desirable that the preparation of the present invention be a preparation which remains in the stomach for a certain period of time after entering the stomach without being immediately discharged from the stomach, and in which the surface of the preparation is gradually eroded and disintegrated by the gastric contraction movement, so that the labeled compound containing the isotope is gradually eluted into the stomach as the abovementioned erosive disintegrate occurs. Furthermore, as was described above, the labeled compound that is eluted inside the stomach may be immediately converted into labeled carbon dioxide gas inside the stomach, or may be absorbed and metabolized by the intestines or liver, depending on the type of compound that is used, resulting in discharging in the exhalation as labeled carbon dioxide gas.

It is sufficient if the stomach-soluble preparation of the present invention is a preparation that shows the abovementioned disintegrate and elution behavior, there are no restrictions on the form of the preparation, components other than the labeled compound, proportions at which the respective components are mixed, or method used to prepare the preparation. Examples of formulations and components other than the labeled compound are indicated below; however, the stomach-soluble preparation of the present invention is not limited in any way by these examples.

A preparation with a particle diameter which will not pass through the pylorus of the stomach, e.g., a particle diameter greater than 1 to 2 mm, may be cited as an example of a preparation that is not immediately discharged form the stomach after entering the stomach. In concrete terms, a preparation with a particle diameter of 5 to 10 mm (and in some cases 2 to 30 mm) can ordinarily be used. However, the present invention is not limited to this particle size range.

For example, even a preparation which has a particle size that is smaller than 1 to 2 mm at administration may be used if this preparation absorbs moisture such as body fluids or the like inside the stomach and thus expands or swells to a size that will not pass through the pylorus of the stomach. Such a preparation can be prepared to contain a substance that has the effect of absorbing moisture and swelling, in addition to the labeled compound. Examples of such swelling substances include gelatin, hydrogel and reaction products of gelatin and N-acetyl-homocysteinethiolactone or the like; all substances of this type that are known in the art may be used. Such swelling substances may be used singly, or may be used in combinations consisting of two or more substances.

In order to prepare a preparation that shows zero-order elution behavior, for example a preparation in which the surface of the preparation is gradually eroded and disintegrated by the gastric contraction movement, it is desirable to use a anti-disintegrator in the preparation, in addition to the labeled compound.

Examples of anti-disintegrators that can be used include all components that are known in the art. For example, water-soluble high-molecular weight compound that are generally known as anti-disintegrators may be widely used. Concrete examples of such water-soluble high-molecular weight compound include water-soluble polymer such as hydroxypropylcellulose, hydroxypropylmethylcellulose, ethylcellulose, cellulose acetate phthalate and the like; the acid-soluble high-molecular weight compoud such as methyl methacrylate-butyl methacrylate-dimethylaminoethyl methacrylate copolymers (e.g., aminoacryl methacrylate copolymer E (commercial name: Oidragit E100, Ream Pharma)), polyvinylacetyl diethylacetate (commercial name: AEA, Sankyo); and weak-alkali-soluble high-molecular weight compound such as acrylic acid copolymers or methacrylic acid copolymers (e.g., methacrylic acid-methyl methacrylate copolymers (commercial name: Oidragit S100, Ream Pharma)), hydroxypropylmethylcellulose acetate succinate (commercial name: AQOAT, manufactured by Shin-Etsu Chemical Co.,Ltd.), carboxymethylethylcellulose, cellulose acetate phthalate and the like. These water-soluble high-molecular weight compound may be used singly, or may be used in arbitrary combinations consisting of two or more polymers. Hydroxypropylcellulose, hydroxypropylmethylcellulose, ethylcellulose and cellulose acetate phthalate are desirable for use, and hydroxypropylcellulose and hydroxypropylmethylcellulose are especially desirable for use.

Furthermore, fats may be cited as examples of anti-disintegrators. Concrete examples of such fats include glycerides that are esters of glycerol with fatty acids such as stearic acid, palmitic acid or the like; cocoa butter, hydrogenated oils, hardened oils, carnauba wax and the like. Furthermore, sugars may also be cited as examples of anti-disintegrators. Examples of such sugars include sucrose, white sugar, corn syrup and the like, and sugar alcohols such as sorbitol, mannitol and the like. These anti-disintegrators may be used singly, or may be used in arbitrary combinations consisting of two or more agents.

There are no particular restrictions on the amount of anti-disintegrator that is contained in the stomach-soluble preparation of the present invention, as long as the effect of the present invention can be manifested. For example, in cases where a water-soluble high-molecular weight compound is used, it is ordinarily desirable that the amount of anti-disintegrator used be in the range of 10 to 90 parts by weight, preferably 20 to 80 parts by weight per 100 parts by weight of the stomach-soluble preparation. Furthermore, in cases where fat and oil are used, it is ordinarily desirable that that the amount of anti-disintegrator used be in the range of 1 to 90 parts by weight, preferably 2 to 60 parts by weight per 100 parts by weight of the stomach-soluble preparation, and in cases where a sugar is used, it is ordinarily desirable that the amount of anti-disintegrator used be in the range of 50 to 99 parts by weight, preferably in the range of 80 to 99 parts by weight per 100 parts by weight of the stomach-soluble preparation.

There are no particular restrictions on the form of the stomach-soluble preparation of the present invention, as long as this preparation is solid. For example, the preparation may take the form of tablets, pills, stomach-soluble capsules, granules, powders or the like. Furthermore, in cases where granules and powders are used, it is desirable to construct the preparation so that the granules and powders swell by absorbing moisture inside the stomach, and thus is not immediately dissolved or discharged from the stomach, but is gradually dissolved and disintegrated from the swollen surfaces by the gastric contraction movement.

Furthermore, the same is true in the case of stomach-soluble capsules filled with granules or a powder. Tablets or pills may be uncoated; alternatively, their surfaces may be coated by a stomach-soluble coating.

In the stomach-soluble preparation of the present invention, all types of carriers and additives ordinarily used in the art may be added as other components in accordance with the form of the preparation, as long as they cause no loss of the action or effect of the present invention. For example, the preparation of the present invention may be a composition prepared by adding a excipient such as lactose, sucrose (white sugar), sodium chloride, glucose, urea, starch, calcium carbonate, kaolin, crystalline cellulose, silicic acid or the like; binders such as simple syrup, liquid glucose, liquid starch, gelatin solution, carboxymethylcellulose, shellac, methylcellulose, potassium phosphate, polyvinylpyrrolidone or the like; integrators such as dried starch, sodium alginate, powdered agar, powdered laminaran, polyoxyethylene sorbitan fatty acid esters, sodium laurylsulfate, stearic acid monoglycerides, starch, lactose and the like; absorbefacients such as quaternary ammonium bases, sodium laurylsulfate and the like; humectants such as glycerol, starch and the like; lubricant such as refined talc, stearates, powdered boric acid, polyethylene glycol and the like; and other additives (e.g., corrigents, flavoring agents, sweeteners, stabilizing agents and the like).

The stomach-soluble preparation for measuring the gastric emptying rate provided by the present invention is ordinarily administered to the subject together with water, and acts as follows in accordance with the kind of labeled compound that is used.

For example, in cases where the labeled compound is $NaH^{13}CO_3$, which quickly appears as labeled carbon dioxide gas in the exhalation following dissolution inside the stomach, the administered preparation is rubbed by the endogastric wall as a result of the gastric contraction (gastric peristalsis), so that the surface of the preparation is scraped away and the preparation is physically pulverized, thus gradually reducing the size of the preparation until the preparation is finally discharged from the pylorus. As the tablet is reduced in size, the isotope-labeled compound ($NaH^{13}CO_3$) is successively eluted from the tablet, and as this compound is eluted, labeled carbon dioxide gas $^{13}CO_2$ is successively excreted in the exhalation. The excretion behavior of the $^{13}CO_2$ gas in the exhalation (this behavior is indicated by the ratio of $^{13}CO_2$ gas to $^{12}CO_2$ gas excreted in the exhalation, i.e., $[^{13}CO_2/^{12}CO_2]$) in cases where the stomach-soluble preparation of the present invention is administered is characterized by the following: specifically, on the basis of the elution characteristics that are peculiar to this preparation, the rise of the $^{13}CO_2$ elimination rate (initial rate) is significantly slower than in a case where a solution of $NaH^{13}CO_3$ is administered, and this rate shows a substantially steady state (plateau state) for a certain period of time after a period of time has elapsed.

For example, the amount of $^{13}CO_2$ at a specified time in the steady state, the $CO_2$ Δ value (%), which is the difference in the δ $^{13}C$ value (%) (i.e., the $^{13}CO_2/^{12}CO_2$ concentration ratio in the exhalation) between the exhalation sample collected before administration of the preparation and each of the exhalation samples collected after administration of the preparation, or the initial rate can be used as an indicator of the gastric emptying rate. For example, a diagnosis of a drop in the gastric emptying function can be made in cases where a subject shows a lower carbon dioxide gas Δ value (%) or initial rate than that of a healthy subject, which is used as a standard.

Furthermore, in cases where the labeled compound is an organic acid such as acetic acid or the like or an amino acid such as glycine or the like, this compound appears in the expired air as labeled carbon dioxide gas after being dissolved inside the stomach, absorbed in the intestines and metabolized by the liver; accordingly, detection of the labeled $CO_2$ is slower than in the case described above. However, since the rate-limiting stage is the dissolution stage of the tablets inside the stomach, excretion behavior similar to that of the abovementioned compounds such as $NaH_{13}CO_3$ and the like is shown.

The preparation for measuring the gastric emptying rate of the present invention may be administered alone, or may be administered together with test food, or immediately before or after feeding. A desirable method is a method in which the preparation for measuring the gastric emptying rate of the present invention is administered immediately after the ingestion of test food.

There are no particular restrictions on the test food used here, as long as the food does not interfere with the action and effect of the preparation of the present invention in measuring the gastric emptying rate. Furthermore, either solid food, fluid food or liquid food may be used; however, solid food is preferable.

(2) Second Preparation (Intestine-Soluble Preparation)

The second preparation of the present invention is a preparation for measuring the gastric emptying rate (intestine-soluble preparation, enteric coated preparation) in which a composition containing a compound that is labeled with either an isotope of C or O, or with isotopes of both, and that is converted into labeled $CO_2$ in the body and excreted in the exhalation, is coated by an enteric coating that dissolves in the intestines.

There are no particular restrictions on the compound labeled with an isotope of C or O or isotopes of both that is used in the abovementioned preparation for measuring the gastric emptying rate, as long as this compound is dissolved inside the intestine following oral administration, and is subsequently disintegrated or metabolized in some cases, and excreted in the exhalation, urine or body fluids (blood, sputum, perspiration or the like).

A desirable example of such a compound is a compound which is converted into carbonate ions ($CO_3^{-2}$), hydrogencarbonate ions ($HCO_3^{-1}$) or carbon dioxide gas ($CO_2$) after being dissolved in the intestine, and after being subsequently disintegrated or metabolized in some cases, and which appears as carbon dioxide gas in the exhalation.

Compounds which dissolve and generate carbonate ions or hydrogencarbonate ions may be broadly cited as examples of compounds that quickly appear as carbon dioxide gas in the exhalation following dissolution; examples of such compounds include alkali metal carbonates such as sodium carbonate, potassium carbonate and the like; alkaline earth metal carbonates such as calcium carbonate, magnesium carbonate and the like; ammonium carbonate; alkali metal hydrogencarbonates such as potassium hydrogencarbonate, sodium hydrogencarbonate and the like; and ammonium hydrogencarbonate. Among these compounds, more preferable are sodium carbonate, potassium carbonate, sodium hydrogencarbonate, and potassium hydrogencarbonate.

These compounds may be used in combination with acidic compounds such as citric acid, tartaric acid, malic acid and the like. In concrete terms, it is possible to hasten the appearance of carbon dioxide gas in the exhalation following oral administration by preparing the abovementioned labeled compound as a single administration in an enteric coated form together with the acidic compound. Furthermore, it is possible to measure the gastric emptying rate with good precision, without affecting the acidity of the stomach of the subject even in cases where the subject tends to hypoacidity, by using an acidic compound as a separately administered preparation in combination with an intestine-soluble preparation containing the abovementioned labeled compound.

Furthermore, amino acids, proteins, organic acids or salts thereof (e.g., alkali metal salts such as Na salts or the like), sugars, fats and the like may be cited as examples of compounds that appear as carbon dioxide gas in the exhalation after being dissolved in the intestine and subsequently disintegrated or metabolized. After being digested and absorbed, all of these compounds generate carbon dioxide gas in the exhalation as a result of liver metabolism. Here, examples of amino acids that can be used include glycine, phenylalanine, tryptophan, methionine, valine, histidine and the like; examples of organic acids that can be used include acetic acid, lactic acid, pyruvic acid, butyric acid, octanoic acid, propionic acid and alkali metal salts of these acids; examples of sugars that can be used include glucose, galactose, xylose, lactose and the like; and examples of fats that can be used include medium-chain triglycerides such as trioctanoin or the like. However, the present invention is not limited to these compounds. Examples of compounds that are especially desirable for use include amino acids such as glycine or the like, organic acids such as acetic acid, octanoic acid or the like, and alkali metal salts of such organic acids (sodium salts or potassium salts).

Concrete examples of isotopes that can be used to label such compounds include $^{13}C$, $^{14}C$ and $^{18}O$. Such isotopes may be radioactive or non-radioactive; however, from the standpoint of safety, non-radioactive isotopes are preferable. In particular, $^{13}C$ is especially desirable for use as such an isotope.

A core of the preparation of the present invention may be prepared using abovementioned labeled compound by itself, or using a composition containing the labeled compound and any desired carriers or additives ordinarily used in this field in accordance with the form of the preparation. Examples of such carriers or additives that can be used include excipients such as lactose, sucrose (white sugar), sodium chloride, glucose, urea, starch, calcium carbonate, kaolin, crystalline cellulose, silicic acid or the like; binders such as simple syrup, liquid glucose, liquid starch, gelatin solution, carboxymethylcellulose, shellac, methylcellulose, potassium phosphate, polyvinylpyrrolidone or the like; disintegrators such as dried starch, sodium alginate, powdered agar, powdered laminaran, polyoxyethylene sorbitan fatty acid esters, sodium laurylsulfate, stearic acid monoglycerides, starch, lactose or the like; absorbefacients such as quaternary ammonium bases, sodium laurylsulfate or the like; humectants such as glycerol, starch and the like; lubricants such as refined talc, stearates, powdered boric acid, polyethylene glycol or the like; and other additives (e.g., corrigents, flavoring agents, sweeteners, stabilizing agents and the like).

The intestine-soluble type preparation for measuring the gastric emptying rate of the present invention is prepared by coated the abovementioned labeled compound or a composition containing this compound with an enteric coating.

There are no particular restrictions on the coated form, as long as the coating is designed so that the coating does not dissolve inside the stomach when the preparation of the present invention is orally administered, and so that the coating dissolves in accordance with the pH inside the intestines after the preparation is discharged from the stomach, with the isotope-labeled compound contained inside being eluted and dissolved at the same time as the dissolution of the coating or following the dissolution of the coating. Examples of such coated forms include a coated preparation in which the surface of the core consisting of the labeled compound or the composition containing the labeled compound, which is prepared in any of various forms such as powders, granules, tablets, pills or the like, is coated with an enteric coating, capsules in which a liquid-form (including emulsions and the like), powder-form or granular labeled compound or composition containing such a compound is contained inside a capsule made of an intestine-soluble substance. Furthermore, these coating treatments can be accomplished using ordinary methods.

The term "enteric coating" or "intestine-soluble substance" used in the present invention refers to a substance that dissolves under the weakly acidic to weakly alkaline conditions seen in the pH inside the intestines (more concretely, in a pH range of 4 to 8, and preferably in a pH range of 5 to 7). In concrete terms, examples of such substances include intestine-soluble high-molecular weight compound such as hydroxypropylmethylcellulose phthalate (commercial names: HP-55, HP-50, Shin-Etsu Chemical Co., Ltd.), acrylic acid copolymers or methacrylic acid copolymers (e.g., methacrylic acid-methyl methacrylate copolymers (commercial name: Oidragit S100, Ream Pharma) or the like), hydroxypropylmethylcellulose acetate succinate (commercial name: AQOAT, Shin-Etsu Chemical Co., Ltd.), carboxymethylethylcellulose, hydroxypropylmethylcellulose phthalate, cellulose acetate phthalate and the like.

The intestine-soluble preparation of the present invention can be appropriately designed and prepared in accordance with the manner of use of the preparation, the time of administration and the like.

For example, in cases where the gastric emptying rate is measured for fasting subjects, i.e., subjects with an empty stomach, it is desirable that the preparation be designed and prepared so that the final size of the preparation is a specified size or greater.

Here, the term "specified size" used in reference to the preparation refers to a size which is such that in cases where the preparation is orally administered, the preparation remains inside the stomach for a certain period of time without being immediately discharged from the stomach, and is only discharged from the stomach by the phase III excretory wave in the fasting mode, i.e., the housekeeper wave.

There are no particular restrictions on the size of the preparation of the present invention, as long as the preparation has a size which is such that the preparation substantially shows the abovementioned behavior in the stomach and intestines. In concrete terms, this includes a preparation with a mean size of approximately 0.1 mm or greater (in some cases approximately 0.5 mm or greater, in some cases approximately 1 mm or greater, and in some cases approximately 2 mm or greater). However, the present invention is not limited to such sizes. Furthermore, from the standpoint of practical use, a mean size of approximately 30 mm may be cited as an example of the upper limit of the preparation size; however, the present invention is not restricted to such a limit.

Furthermore, the intestine-soluble preparation of the present invention is not limited to a preparation that already has a desired size at the time of administration, but may also be a preparation which swells to a desired size as a result of absorbing moisture such as body fluids or the like following administration.

As was described above, the intestine-soluble preparation of the present invention is coated by an enteric coating, so that the preparation does not dissolve or disintegrate in the stomach. Accordingly, when a preparation having the abovementioned size is orally administered to a subject under fasting conditions, this preparation shows the following behavior: specifically, in a fasting mode, after remaining inside the stomach for a certain period of time, the preparation is finally discharged into the intestines from the stomach by a strong contractile movement that pushes the stomach contents toward the pylorus as a result of the appearance of the housekeeper wave. Once the preparation has been discharged into the intestines, the enteric coating on the surface of the preparation is dissolved by the effects of the pH inside the intestines, so that the labeled compound inside the preparation begins to be eluted. Here, the labeled compound $NaH^{13}CO_3$ quickly appears as labeled carbon dioxide gas in the exhalation after being dissolved in the intestines. For example, in a case where the preparation contains such a labeled compound $NaH^{13}CO_3$, the labeled compound is eluted inside the intestines, and as the compound dissolves, labeled carbon dioxide gas $^{13}CO_2$ is successively excreted in the exhalation.

The excretion behavior of the $^{13}CO_2$ gas in the exhalation (in concrete terms, this behavior is indicated by the ratio of $^{13}CO_2$ gas to $^{12}CO_2$ gas excreted in the exhalation, i.e., [$^{13}CO_2/^{12}CO_2$]) ordinarily shows an abrupt rise pattern based on the gastric excretion movement that is peculiar to the subject, especially the housekeeper excretion in phase III. The housekeeper wave ordinarily appears periodically every 1 to 3 hours under fasting conditions; however, in the case of subjects in which there is a drop in the gastric emptying rate, as in diabetic patients and the like, the appearance of this housekeeper wave may be delayed, weakened or completely absent. Accordingly, in the case intestine-soluble preparation of the present invention, the presence or absence of any drop in gastric emptying function can be evaluated by measuring the amount of $^{13}CO_2$ gas over time following oral administration, or more concretely the $CO_2$ $\Delta$ value (%) (i.e., the difference between the $\delta$ $^{13}C$ value ($^{13}CO_2/^{12}CO_2$ concentration ratio in the exhalation) in each of the exhalation samples collected following administration and the $\delta$ $^{13}C$ value in the exhalation sample prior to administration).

Furthermore, in cases where the labeled compound is an organic acid such as acetic acid or the like or an amino acid such as glycine or the like, this compound appears as labeled carbon dioxide gas in the exhalation after being dissolved and absorbed in the intestines and metabolized by the liver. Accordingly, detection thereof (the labeled $^{13}CO_2$ gas excreted in the exhalation) is slower than in the case described above. However, since the rate-limiting stage is the excretory from the stomach by the housekeeper wave, the presence or absence of a drop in the gastric emptying rate can be evaluated in the same manner as in the case of compounds such as the abovementioned $NaH^{13}CO_3$ or the like.

As was described above, the administration of the intestine-soluble preparation of the present invention can be performed under fasting conditions by the administration of a preparation with a specified size alone; however, this preparation can also be administration together with food such as test food or the like, or immediately prior to or following the ingestion of test food.

Specifically, in the present invention, the gastric emptying rate can also be measured for subjects who have ingested food.

In this case, it is desirable that the preparation be designed and prepared so that the final size of the preparation is smaller than the size. Here, the term "specified size" refers to a size which is such that in cases where the preparation with the size is orally administered, the preparation is discharged from the stomach by the gastric movement to discharge food, after entering the stomach.

There are no particular restrictions on the size of the preparation of the present invention, as long as the preparation has a size which is such that the preparation substantially shows the abovementioned behavior in the stomach and intestines. In concrete terms, this includes a preparation with a mean size of approximately 5 mm or less (in some cases approximately 2 mm or less, in some cases approximately 1 mm or less, and in some cases approximately 0.5 mm or less). However, the present invention is not limited to such sizes.

Food that has entered the stomach is physically pulverized by gastric contraction (gastric peristalsis) so that this food is gradually reduced in size, and when the food has been reduced to a specified size, the food is discharged from the pylorus. In the case of the abovementioned intestine-soluble preparation of the present invention, when the preparation is administered in such ingestion mode, the preparation remains inside the stomach for a certain period of time together with the food, and is then discharged into the intestines together with the food when the food has been reduced to a specified size. In the preparation that has been discharged into the intestines, the enteric coating on the surface is dissolved by the effects of the pH in the intestines, so that the labeled compound is eluted from the inside, and is successively excreted in the exhalation as labeled carbon dioxide gas, either immediately following the dissolution of the compound, or after metabolization of the compound in the body. In other words, the excretion behavior of the labeled carbon dioxide gas according to the intestine-soluble preparation of the present invention reflects the gastric emptying pattern that is peculiar to each subject in the ingestion mode; accordingly, the gastric emptying function of the subject can be evaluated from such excretion behavior of the carbon dioxide gas.

Here, there are no particular restrictions on the food that is ingested together with the preparation, as long as the food does not interfere with the action and effect of the preparation of the present invention in measuring the gastric emptying rate. Furthermore, either solid food, fluid food or liquid food may be used. Moreover, by appropriately selecting the food (test food) that is ingested together with the preparation, it is possible to investigate and confirm more detailed gastric emptying functions and gastric motor mechanisms.

(3) Method for Measuring the Gastric Emptying Rate

The present invention also provides a method for measuring the gastric emptying rate using the abovementioned preparations for measuring the gastric emptying rate (stomach-soluble preparation and intestine-soluble preparation). Measurement of the gastric emptying rate can be accomplished by administering the preparation of the present invention for measuring the gastric emptying rate (stomach-soluble preparation or intestine-soluble preparation) containing the abovementioned labeled compound to living animals or humans, collecting the exhalation, urine, feces, blood or other body fluids, and preferably the exhalation, and investigating the behavior of the compound in the body form the amount of the labeled compounds that is excreted in the collected samples.

For example, in cases where the exhalation is used as the collected sample and $^{13}C$ is used as the isotope, the gastric emptying rate can be measured by orally administering the preparation of the present invention for measuring the gastric emptying rate (stomach-soluble preparation or intestine-soluble preparation) to the subject, collecting samples of the exhalation over time, and measuring the the amount of $^{13}CO_2$ excreted in the exhalation over time as the ratio of $^{13}CO_2/^{12}CO_2$ ($\delta$ $^{13}C$ value), according to $^{13}C$ exhalation examination methods.

In the case of the preparation for measuring the gastric emptying rate of the present invention, both the stomach-soluble preparation and intestine-soluble preparation are unaffected by physiological factors such as absorption or metabolization in cases where a compound that dissolves and generates carbonate ions or hydrogencarbonate ions such as sodium hydrogencarbonate or the like is used as the labeled compound. Accordingly, measurements that directly reflect the gastric movement (gastric peristalsis) can be made. Furthermore, physiological reactions (gastric emptying functions) can be investigated in greater detail by testing with the test food varied (e.g., by loading with fats or the like).

Furthermore, evaluation of the gastric emptying rate can be accurately performed with much greater precision by performing repeated administration of the stomach-soluble preparation or intestine-soluble preparation of the present invention instead of a single administration, or by performing such administration a multiple number of times under different conditions such as fasting conditions and ingestion conditions or the like. In addition, the gastric emptying function can be evaluated with a higher degree of precision by performing an evaluation that combines both the results obtained by measuring the gastric emptying rate using the stomach-soluble preparation and the results obtained by measuring the gastric emptying rate using the intestine-soluble preparation.

The measurement and analysis of the labeled compound contained in the collected samples vary according to whether the isotope used is radioactive or non-radioactive; however, such analysis can be performed using commonly used analysis methods such as the liquid scintillation counter method, mass analysis method, infrared spectroscopic analysis method, emission spectrochemical analysis method, magnetic resonance spectrum method or the like. From the standpoint of measurement precision, the infrared spectroscopic analysis method and mass analysis method are especially desirable.

The method used to administer the preparation of the present invention for measuring the gastric emptying rate (stomach-soluble preparation or intestine-soluble preparation) is as described above; however, there are no particular restrictions on this method.

The amount of labeled compound that is contained in an administration unit of the preparation of the present invention varies according to the sample being measured and the type of labeled compound used, and therefore cannot be set as a specific value. This amount can be appropriately adjusted and set on a case by case basis. For example, in both the first preparation and the second preparation, in cases where measurement is performed by an exhalation test using sodium hydrogencarbonate ($NaH^{13}CO_3$) as the labeled compound, it is desirable that the preparation contain 1 to 2000 mg, and preferably 10 to 200 mg, of sodium hydrogencarbonate ($NaH^{13}CO_3$) per unit administration. Furthermore, in cases where measurement is performed by a exhalation test using acetic acid ($CH_3^{13}COOH$) as the labeled compound, it is desirable that the preparation contain 1 to 200 mg, and preferably 10 to 200 mg, of acetic acid per unit administration.

A reduction or acceleration of the gastric emptying rate in the subject can be diagnosed and evaluated by utilizing the abovementioned method for measuring the gastric emptying rate. In concrete terms, such a diagnosis can be accomplished by comparing the behavior of the labeled compound in the body or the amount or behavior of a labeled compound excreted from the body measured for a subject by the abovementioned method with a standard control (behavior of the labeled compound in the body or the amount or behavior of a labeled compound excreted from the body measured for a healthy subject).

For example, the gastric emptying rate of a subject can be diagnosed and evaluated by administering the preparation of the present invention for measuring the gastric emptying rate (stomach-soluble preparation or intestine-soluble preparation) to the subject, measuring the amount of labeled carbon dioxide gas ($^{13}CO_2$) that is excreted in the exhalation following this administration, or the $CO_2$ Δ value (‰) (i.e., the difference between the δ $^{13}C$ value following administration of the preparation and the δ $^{13}C$ value prior to administration of the preparation), over time, and comparing the resultant excretion pattern for the subject with that for a standard control (healthy subject).

Furthermore, as was described above, the first preparation of the present invention, i.e., the stomach-soluble preparation for measuring the gastric emptying rate, is characterized by the fact that the amount of labeled carbon dioxide gas ($^{13}CO_2$) or the $CO_2$ Δ value (%) maintains a plateau state after a certain period of time has elapsed. Accordingly, in cases where the first preparation is used, the gastric emptying rate of the subject can also be diagnosed and evaluated using the method described below instead of the method described above. First, the gastric emptying rate of a healthy subject is measured beforehand as described above, and the resulting behavior over time is used as a standard control. Next, the same preparation for measuring the gastric emptying rate is administered to a subject for whom a drop in the gastric emptying rate is suspected, such as a subject suffering from the abovementioned indefinite complaint, and the amount of 13CO_2 or the $CO_2$ Δ value (%) in the exhalation sample, which is collected at least one point in time positioned in the plateau state of the standard control, is measured. In this case, the presence or absence of a drop in the gastric emptying rate can be evaluated according to whether the $CO_2$ Δ value (%) of the subject is higher or lower than that of the standard control. Such a method is useful in that the gastric emptying rate can be simply evaluated by collecting a small number of exhalation samples without constraining the subject for a long period of time. Furthermore, the presence or absence of a drop in the gastric emptying rate can also be evaluated from the initial rate of $^{13}CO_2$ excreted in the exhalation. If this method is used, the time for which the subject is constrained can be greatly shortened. In this case, it may be judged that there has been a drop in the gastric emptying rate in cases where the initial rate of $^{13}CO_2$ excreted in the exhalation that is measured for the subject is slower than the initial rate of $13CO_2$ measured for the standard control.

Furthermore, by using such a method for measuring the gastric emptying rate, it is possible to the pharmacological effects of drugs relating to the gastric motor function, and the therapeutic effects of such drugs on individual subjects. In concrete terms, such an evaluation can be performed by measuring the gastric emptying rate using the preparation of the present invention for measuring the gastric emptying rate before and after the administration of s drug relating to the gastric motor function to the subject, and comparing the respective results. In this way, the pharmacological effect of the abovementioned drug itself can be evaluated. Furthermore, the therapeutic effects of individual drugs on the subject can also be evaluated. As a result, this method can also be used as a means of selecting drugs that are suited to individual subjects. Furthermore, drugs having effects that forcibly adjust the gastric peristalsis movement in an accelerating or inhibitory manner, such as gastric motor function enhancers, gastric motor function accelerators or gastric motor function suppressers may be cited as examples of drugs relating to the gastric motor function.

EXAMPLES

The present invention will be described more thoroughly below in terms of examples and test examples. However, the present invention is not limited in any way by these examples.

Example 1

Stomach-Soluble Preparation

| | |
|---|---|
| Sodium hydrogencarbonate ($NaH^{13}CO_3$) | 100 mg |
| Hydroxypropylcellulose (HPC-L, Shin-Etsu Chemical Co., Ltd.) | 50 mg |
| Magnesium stearate | 1 mg |
| Total | 151 mg |

A disintegrate-release type sustained-release tablet with a diameter of 10 mm was prepared using ordinary methods by mixing the abovementioned components. When this preparation was subjected to an in vitro elution test (according to the 13$^{th}$ revised Japan Pharmacopoeia), it was confirmed that the preparation showed zero-order release behavior.

Example 2

Stomach-Soluble Preparation

| | |
|---|---|
| Sodium hydrogencarbonate (NaH$^{13}$CO$_3$) | 100 mg |
| Lactose | 40 mg |
| Hydroxypropylmethylcellulose | 40 mg |
| Magnesium stearate | 2 mg |
| Total | 182 mg |

A disintegrate-release type sustained-release tablet with a diameter of 10 mm was prepared using ordinary methods by mixing the abovementioned components.

Example 3

Stomach-Soluble Preparation

| | |
|---|---|
| Sodium hydrogencarbonate (NaH$^{13}$CO$_3$) | 100 mg |
| Lactose | 40 mg |
| Hydroxypropylcellulose (HPC-L, Shin-Etsu Chemical Co., Ltd.) | 40 mg |
| Magnesium stearate | 2 mg |
| Total | 182 mg |

A disintegrate-release type sustained-release tablet with a diameter of 10 mm was prepared using ordinary methods by mixing the abovementioned components.

Example 4

Stomach-Soluble Preparation

| | |
|---|---|
| Sodium hydrogencarbonate (NaH$^{13}$CO$_3$) | 100 mg |
| Hydroxypropylcellulose (HPC-L, Shin-Etsu Chemical Co., Ltd.) | 80 mg |
| Magnesium stearate | 2 mg |
| Total | 182 mg |

A disintegrate-release type sustained-release tablet with a diameter of 10 mm was prepared using ordinary methods by mixing the abovementioned components.

Example 5

Stomach-Soluble Preparation

| | |
|---|---|
| Sodium hydrogencarbonate (NaH$^{13}$CO$_3$) | 100 mg |
| Lactose | 20 mg |
| Hydroxypropylcellulose (HPC-L, Shin-Etsu Chemical Co., Ltd.) | 60 mg |
| Magnesium stearate | 2 mg |
| Total | 182 mg |

A disintegrate-release type sustained-release tablet with a diameter of 10 mm was prepared using ordinary methods by mixing the abovementioned components.

Example 6

Stomach-Soluble Preparation

| | |
|---|---|
| Sodium hydrogencarbonate (NaH$^{13}$CO$_3$) | 100 mg |
| Lactose | 82 mg |
| Hardened oil (Lubri Wax-101, Freund Industrial Co., Ltd.) | 16 mg |
| Magnesium stearate | 2 mg |
| Total | 200 mg |

A disintegrate-release type sustained-release tablet with a diameter of 8 mm (thickness 2.5 mm, hardness 5 kp) was prepared by mixing the abovementioned components using an ordinary dry granulation method.

Example 7

Stomach-Soluble Preparation

| | |
|---|---|
| Sodium hydrogencarbonate (NaH$^{13}$CO$_3$) | 100 mg |
| Lactose | 78 mg |
| Hardened oil (Lubri Wax-101, Freund Industrial Co., Ltd.) | 20 mg |
| Purified water | 40 mg |
| Magnesium stearate | 2 mg |
| Final weight of tablet (solid content) | 200 mg |

A disintegrate-release type sustained-release tablet with a diameter of 8 mm was prepared by mixing the abovementioned components using an kneading granulation method.

Example 8

Intestine-Soluble Preparation

| | |
|---|---|
| <Core Components> | |
| Sodium hydrogencarbonate (NaH$^{13}$CO$_3$) | 100 mg |
| Refined white sugar (powdered) | 150 mg |
| Corn starch | 100 mg |
| Crystalline cellulose (Avicel PH-301, Asahi Kasei) | 100 mg |
| Calcium carboxymethylcellulose (ECG-5-5, Nichirin Chemical Co., Ltd.) | 50 mg |
| Hydroxypropylcellulose (HPC-L, Shin-Etsu Chemical Co., Ltd.) | 7.5 mg |
| Purified water | 75 mg |
| Anhydrous ethanol | 67.5 mg |
| Total solid content | 507.5 mg |
| <Enteric Coating Liquid Components> | |
| Hydroxypropylmethylcellulose phthalate (HP-55, Chin-Etsu Chemical Co., Ltd.) | 6.0 mg |
| Talc | 1.8 mg |
| Anhydrous ethanol | 73.8 mg |
| Purified water | 18.4 mg |
| Total | 100.0 mg |

Using labeled sodium hydrogen carbonate (NaH$^{13}$CO$_3$) as an active ingredient, the respective ingredients were mixed and bonded in accordance with the composition of the abovementioned <Core Components>, and granules were manufactured by an ordinary method. Next, these core granules were spray-coated with the enteric coating liquid having the composition described above, thus producing granules that were coated with hydroxypropylmethylcellulose phthalate which is an enteric coating, at the rate of 40 parts by weight per 100 parts by weight of the granules. Furthermore, the mean particle size of these granules was 1000 to 1400 μm.

Example 9

Intestine-Soluble Preparation

Granules for making tablet were manufactured according an ordinary method by using 50 mg of labeled sodium acetate ($CH_3{}^{13}COONa$) as an active gredient, and mixing an excipient (lactose, corn starch 50 mg), a binder (hydroxypropylmethylcellulose 50 mg), a disintegrator (crystalline cellulose 25 mg) and a lubricant (magnesium stearate 3 mg). These granules were compressed to produce a tablet containing 50 mg of $CH_3{}^{13}COONa$ according to an ordinary method. Next, this tablet was coated with an enteric coating (hydroxypropylmethylcellulose phthalate (commercial name: HP-55, Shin-Etsu Chemical Co., Ltd.) (proportion of coating layer: 2 wt % in 100 wt % of the tablet), thus producing an intestine-soluble preparation containing $CH_3{}^{13}COONa$ (diameter: approximately 7 mm).

TEST EXAMPLES

Test Example 1

An elution test was performed in accordance with the elution test method (paddle method) of the Japan Pharmacopoeia ($13^{th}$ Ed.) for the sustained-release tablet of Example 6 in order to evaluate the elution behavior of this tablet in the body. In concrete terms, 10 tablets of the sustained-release tablet (Example 6) were placed in a test vessel containing a test solution (acetic acid-ammonium acetate buffer solution (pH 4.8) 500 mL, 37±0.5° C.), the paddle rpm was set at 200 rpm or 75 rpm, and the elution behavior of the tablet at the respective rpm values was observed by measuring the solubility (%) over time. The results obtained are shown in FIG. 1. Furthermore, in order to evaluate the elution behavior in case where the sustained-release tablet of the present invention is administered at feeding, an elution test was similarly performed in which 100 g or 200 g of beads (Diapet ABS X-0119, 1400 μm ON, specific gravity 1.05, Mitsubishi Rayon) were placed in the test vessel in addition to 10 tablets of the sustained-release tablet (Example 6). These results are shown respectively in FIGS. 2 and 3.

It was confirmed from these results that the sustained-release tablet of the present invention shows significantly different elution behavior (solubility) according to the paddle rpm imitated for the gastric emptying movement, with the elution behavior (solubility) showing a higher value at an increased rpm, and a lower value at a reduced rpm (FIG. 1). Furthermore, it was confirmed that the difference in the elution behavior is more conspicuous in the presence of beads that mimic an ingestion state (FIGS. 2 and 3). This means specifically that in the case of the sustained-release tablet of the present invention, a drop (or acceleration) in the gastric motor function can be evaluated by a delay (or acceleration) of the rate of elution of the labeled compound into the exhalation that is connected with a drop (or rise) in the elution behavior of the tablet in the stomach.

This indicates a possibility that exhalation tests using stomach-soluble preparation (disintegrate-release type sustained-release preparation) of the present invention can monitor the gastric emptying rate (gastric motor function), and therefore may be very useful in performing accurate diagnoses and selecting appropriate methods for subjects suffering from indefinite complaints caused by a drop in the gastric emptying rate.

Test Example 2

The gastric emptying rate was evaluated using the intestine-soluble granules prepared in Example 8. In concrete terms, ⅛ ounce capsules (long diameter: approximately 13 mm, short diameter: approximately 5 mm) were filled with the intestine-soluble granules of Example 8 so that each capsule contained 100 mg of sodium hydrogencarbonate ($NaH^{13}CO_3$), and these capsules were forcibly orally administered to fasting male beagle dogs (n=4, referred to below as untreated group or gastric emptying normal model) as a preparation for measuring the gastric emptying rate. Following this oral administration, the pH inside the stomach was immediately adjusted by the forcible administration of 20 mL of 0.1 N aqueous solution of hydrochloric acid. Next, exhalation samples were collected over time at 15-minute intervals, and the carbon dioxide gas concentration ratio ($_{13}CO_2/{}^{12}CO_2$ concentration ratio: δ $^{13}C$ value) in the exhalation at each collection time was measured using gas chromatography (GC-MS) (ABCA-G, Europa Scientific). The carbon dioxide gas Δ value (%) was calculated from the difference between the δ $^{13}C$ value at the time of the collection of each sample and the δ $^{13}C$ value measured prior to the administration of the capsules (δ $^{13}C$ value following capsule administration—δ $^{13}C$ value prior to capsule administration).

Furthermore, as a control test, a sodium hydrogencarbonate solution (containing 100 mg of $NaH^{13}CO_3$) was administered to male beagle dogs (n=4) instead of the abovementioned capsule; the carbon dioxide gas concentration ratio (δ $^{13}C$ value) in the exhalation was similarly measured over time, and the carbon dioxide gas Δ value (%) was calculated. Furthermore, a gastric emptying delay model was artificially created by separately administering an anti-choline agent (propantheline) to male beagle dogs (n=4). Then, the abovementioned capsule was administered to the animals of the stomach elimination retardation model (group receiving propantheline), after which the carbon dioxide gas concentration ratio (δ $^{13}C$ value) in the exhalation was similarly measured over time, and the carbon dioxide gas Δ value (%) was calculated.

Figure 4:
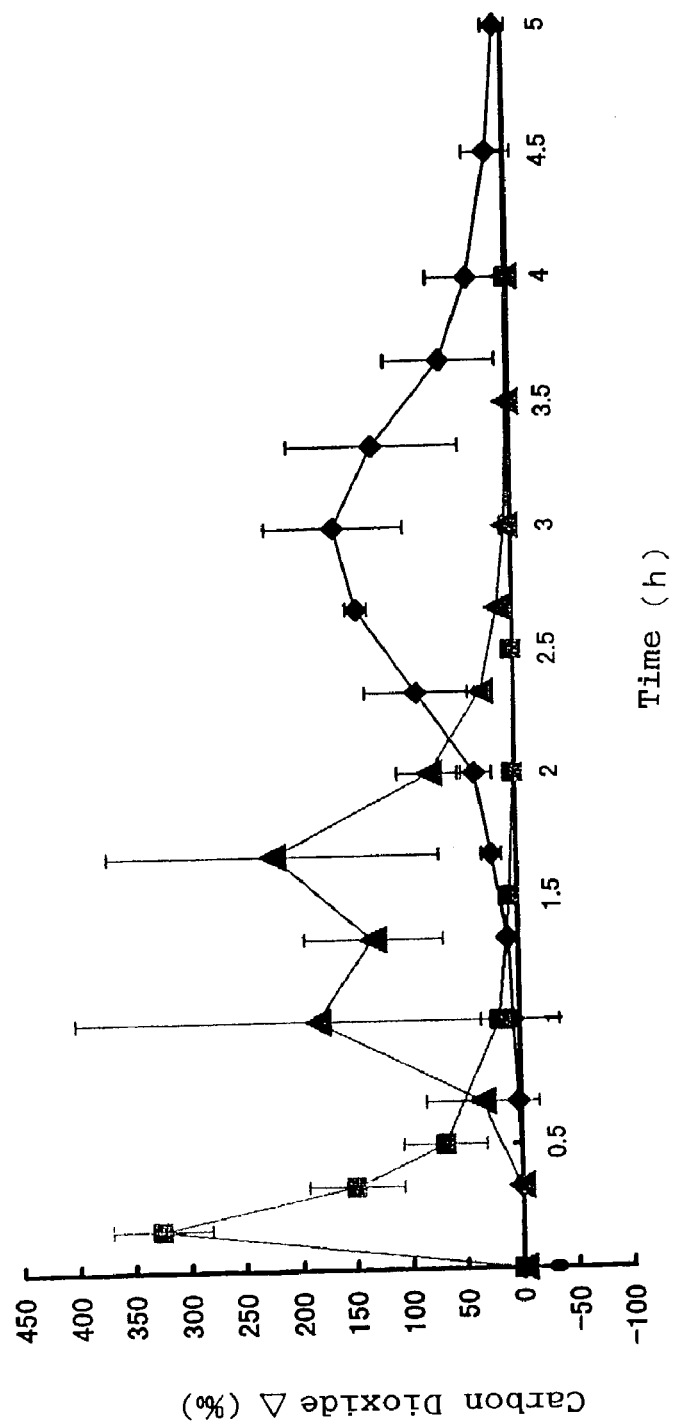
FIG. 4 is a graph which shows the results obtained in Test Example 2. Specifically, this graph shows the average exhalation pattern for four beagle dogs that were given the capsule enclosed enteric coated granules of the present invention (closed triangles, -▲-) or an aqueous solution of sodium hydrogen carbonate ($NaH^{13}CO_3$ solution) (closed squares, -■-), with the time elapsed following administration being shown in the horizontal axis and the $CO_2$ Δ value (%) being shown on the vertical axis. Furthermore, the closed diamond symbols (-♦-) indicate the exhalation pattern obtained in a case where beagle dogs treated in advance with an anti-choline agent (propantheline) (gastric emptying retardation model) were given the capsule enclosed enteric coated granules of the present invention.

The results obtained are shown in FIG. 4. FIG. 4 shows the mean exhalation pattern for four beagle dogs, with the time (h) elapsed following administration being shown on the horizontal axis, and the carbon dioxide gas Δ value (%) being shown on the vertical axis. As is seen from this figure, the sodium hydrogencarbonate solution ($NaH^{13}CO_3$ solution) in the control test showed a maximum of the carbon dioxide gas Δ value (%) immediately after administration, and was then rapidly excreted from the body. On the other hand, the encapsulated enteric coated granules of the present invention showed a maximum value (%) at approximately 1.3 hours (Tmax) following administration, and were excreted relatively slowly. Meanwhile, in the case of the group receiving propantheline (gastric emptying retardation model), the excretion of labeled carbon dioxide gas in the exhalation was slow compared to that seen in the beagle dogs of the untreated group (gastric emptying normal model), with the maximum value (%) reaching at approximately 2.8 hours (Tmax=2.8 hs).

It is clear from these findings that the intestine-soluble preparation of the present invention allows the definite measurement of a drop in the gastric emptying rate in the gastric emptying retardation model on the basis of the delay of the excretion of the labeled carbon dioxide gas in the exhalation. This indicates that the gastric emptying function can be evaluated by measuring the respiratory excretion pattern of the labeled carbon dioxide gas in a exhalation test using the preparation of the present invention.

INDUSTRIAL APPLICABILITY

The preparation of the present invention for measuring the gastric emptying rate makes it possible to measure the gastric emptying function in humans or animals simply and with good precision. Especially if a preparation for measuring the gastric emptying rate prepared using a labeled compound that is excreted in the exhalation as carbon dioxide gas is used, the gastric emptying function can be simply measured by means of an exhalation test without placing a psychological or physical burden on the subject.

Furthermore, by using the preparation of the present invention for measuring the gastric emptying rate, and a method for measuring the gastric emptying rate that employs this preparation, it is possible to diagnose and evaluate a drop or acceleration in the gastric emptying rate of the subject simply and with good precision. Furthermore, by using the preparation of the present invention for measuring the gastric emptying rate, and a method for measuring the gastric emptying rate that employs this preparation, it is possible to evaluate the pharmacological effects of drugs relating to the gastric motor function in a direct and simple manner, and to evaluate the therapeutic effects of such drugs on individual subjects directly, and in an objective manner.

The invention claimed is:

1. A preparation for measuring the gastric emptying rate comprising a composition containing a compound that is labeled with at least one of the isotopes of C and O and that is converted into labeled $CO_2$ in the body and excreted in the exhalation,
   the preparation being coated by an enteric coating and having a mean size of 1 mm or greater, wherein the behavior of the preparation following oral administration to a subject being such that:
   (1) the preparation remains inside the stomach after entering the stomach, without being discharged from the stomach,
   (2) the preparation is discharged from the stomach by the gastric housekeeper movement, and
   (3) the preparation is dissolved in the intestines, and the labeled compound eluted from the interior of the preparation is converted into labeled carbon dioxide inside the intestines or absorbed and metabolized, and is excreted in the exhalation.

2. A preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating that dissolves in the intestines and having a mean size of 2 mm or smaller, wherein the behavior of the preparation following oral administration to a subject being such that:
   (1) the preparation enters the stomach,
   (2) the preparation is discharged from the stomach by the gastric movement to discharge food, and
   (3) the preparation is dissolved in the intestines, and the labeled compound eluted from the interior of the preparation is converted into labeled carbon dioxide inside the intestines or absorbed and metabolized, and is excreted in the exhalation.

3. The preparation for measuring the gastric emptying rate according to claim 1, wherein the isotope is at least one member selected from a group consisting of $^{13}C$, $^{14}C$ and $^{18}O$.

4. The preparation for measuring the gastric emptying rate according to claim 1, wherein the labeled compound is at least one member selected from a group consisting of alkali metal salt, alkaline earth metal salt and ammonium salt of carbonic acid and alkali metal hydrogencarbonate, alkaline earth metal hydrogencarbonate and ammonium hydrogencarbonate.

5. The preparation for measuring the gastric emptying rate according to claim 1, wherein the labeled compound is at least one member selected from a group consisting of acetic acid, glycine, octanoic acid and alkali metal salts thereof.

6. A method for measuring the gastric emptying rate, which comprises orally administering the preparation for measuring the gastric emptying rate according to any of claim 1 or 2 to a subject, and measuring the behavior of the labeled compound inside the body or the amount or rate of a labeled compound excreted from the body.

7. A method for measuring the gastric emptying rate, comprises orally administering the preparation for measuring the gastric emptying rate according to any of claim 1 or 2 to a subject, and measuring the amount or rate of labeled $CO_2$ excreted in the exhalation.

8. A method for evaluating the gastric emptying rate of a subject for whom a reduction or acceleration of the gastric emptying rate is suspected, comprising the steps of:
   orally administering the preparation for measuring the gastric emptying rate according to any of claim 1 or 2 to said subject; and
   comparing the behavior of the labeled compound inside the body or the amount or rate of a labeled compound excreted from the body with the behavior of the labeled compound inside the body or the amount or rate of a labeled compound excreted from the body obtained for a healthy subject using the same preparation for measuring the gastric emptying rate.

9. A method for evaluating the gastric emptying rate of a subject for whom a reduction or acceleration of the gastric emptying rate is suspected, comprising the steps of:
   orally administering the preparation for measuring the gastric emptying rate according to any of claim 1 or 2 to said subject; and
   comparing the amount or rate of labeled $CO_2$ excreted in the exhalation with the amount or rate of labeled $CO_2$ excreted in the exhalation obtained for a healthy subject using the same preparation for measuring the gastric emptying rate.

10. The method for evaluating the gastric emptying rate according to claim 8, which comprises the steps of
   A) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being a disintegrate-released type sustained-release preparation, and
   B) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating and having a mean size of 1 mm or greater, wherein the behavior of the preparation following oral administration to a subject being such that:
(1) the preparation remains inside the stomach prior to being discharged from the stomach,
(2) the preparation is discharged from the stomach by the gastric housekeeper movement, and
(3) the preparation is dissolved in the intestines, and the labeled compound eluted from the interior of the preparation is converted into labeled carbon dioxide inside the intestines or absorbed and metabolized, and is excreted in the exhalation.

11. A method for evaluating the pharmacological effect of a drug relating to the gastric motor function, or the therapeutic effect of such drug on a subject, comprising the steps of:
orally administering the preparation for measuring the gastric emptying rate according to any of claim 1 or 2 to the subject before and after the administration of a drug relating to the gastric motor function to the subject; and
comparing the behavior of the labeled compound inside the body or the amount or rate of a labeled compound excreted from the body following the administration of said drug with the behavior of the labeled compound inside the body or the amount or rate of a labeled compound excreted from the body prior to the administration of said drug.

12. A method for evaluating the pharmacological effect of drugs relating to the gastric motor function, or the therapeutic effect of such drugs on a subject, comprising the steps of:
orally administering the preparation for measuring the gastric emptying rate according to any of claim 1 or 2 to the subject before and after the administration of a drug relating to the gastric motor function to the subject; and
comparing the amount or rate of labeled $CO_2$ excreted in the exhalation following the administration of said drug with the amount or rate of labeled $CO_2$ excreted in the exhalation prior to the administration of said drug.

13. The method for evaluating the pharmacological effects of a drug relating to the gastric motor function or the therapeutic effects of said drug on a subject according to claim 11, which comprises the steps of
A) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being a disintegrate-released type sustained-release preparation, and
B) an evaluation performed using the preparation for measuring the gastric emptying rate comprising a composition containing a compound that is labeled with at least one of the isotopes of C and O and that is converted into labeled $CO_2$ in the body and excreted in the exhalation,
the preparation being coated by an enteric coating and having a mean size of 1 mm or greater, wherein the behavior of the preparation following oral administration to a subject being such that:
(1) the preparation remains inside the stomach prior to being discharged from the stomach,
(2) the preparation is discharged from the stomach by the gastric housekeeper movement, and
(3) the preparation is dissolved in the intestines, and the labeled compound eluted from the interior of the preparation is converted into labeled carbon dioxide inside the intestines or absorbed and metabolized, and is excreted in the exhalation.

14. A preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating and having a mean size of 2 mm or greater, wherein the behavior of the preparation following oral administration to a subject being such that:
(1) the preparation remains inside the stomach after entering the stomach, without being discharged from the stomach,
(2) the preparation is discharged from the stomach by the gastric housekeeper movement, and
(3) the preparation is dissolved in the intestines, and the labeled compound eluted from the interior of the preparation is converted into labeled carbon dioxide inside the intestines or absorbed and metabolized, and is excreted in the exhalation.

15. A preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating that dissolves in the intestines and having a mean size of 1 mm or smaller, wherein the behavior of the preparation following oral administration to a subject being such that:
(1) the preparation enters the stomach,
(2) the preparation is discharged from the stomach by the gastric movement to discharge food, and
(3) the preparation is dissolved in the intestines, and the labeled compound eluted from the interior of the preparation is converted into labeled carbon dioxide inside the intestines or absorbed and metabolized, and is excreted in the exhalation.

16. The preparation for measuring the gastric emptying rate according to claim 2, wherein the isotope is at least one member selected from a group consisting of $^{13}C$, $^{14}C$ and $^{18}O$.

17. The preparation for measuring the gastric emptying rate according to claim 2, wherein the labeled compound is at least one member selected from a group consisting of alkali metal salt, alkaline earth metal salt and ammonium salt of carbonic acid and alkali metal hydrogencarbonate, alkaline earth metal hydrogencarbonate and ammonium hydrogencarbonate.

18. The preparation for measuring the gastric emptying rate according to claim 2, wherein the labeled compound is at least one member selected from a group consisting of acetic acid, glycine, octanoic acid and alkali metal salts thereof.

19. The method for evaluating the gastric emptying rate according to claim 8, which comprises the steps of
A) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being a disintegrate-released type sustained-release preparation, and B) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating and having a mean size of 2 mm or smaller, wherein the behavior of the preparation following oral administration to a subject being such that:

(1) the preparation remains enters the stomach,
(2) the preparation is discharged from the stomach by the gastric movement to discharge food, and
(3) the preparation is dissolved in the intestines, and the labeled compound eluted from the interior of the preparation is converted into labeled carbon dioxide inside the intestines or absorbed and metabolized, and is excreted in the exhalation.

20. The method for evaluating the pharmacological effects of a drug relating to the gastric motor function or the therapeutic effects of said drug on a subject according to claim 11, which comprises the steps of A) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being a disintegrate-released type sustained-release preparation, and B) an evaluation performed using the preparation for measuring the gastric emptying rate comprising a composition containing a compound that is labeled with at least one of the isotopes of C and O and that is converted into labeled $CO_2$ in the body and excreted in the exhalation, the preparation being coated by an enteric coating and having a mean size of 2 mm or smaller, wherein the behavior of the preparation following oral administration to a subject being such that:

(1) the preparation remains enters the stomach,
(2) the preparation is discharged from the stomach by the gastric movement to discharge food, and
(3) the preparation is dissolved in the intestines, and the labeled compound eluted from the interior of the preparation is converted into labeled carbon dioxide inside the intestines or absorbed and metabolized, and is excreted in the exhalation.

* * * * *